US00PP09998P

United States Patent [19]

Meilland

[11] Patent Number: Plant 9,998

[45] Date of Patent: Aug. 12, 1997

[54] FLORIBUNDA ROSE PLANT NAMED 'MEIOFFIC'

[75] Inventor: Alain A. Meilland, Antibes, France

[73] Assignee: The Conard-Pyle Company, West Grove, Pa.

[21] Appl. No.: 706,494

[22] Filed: Sep. 4, 1996

[51] Int. Cl.[6] ..... A01H 5/00

[52] U.S. Cl. ..... Plt./22

[58] Field of Search ..... Plt./22, 26

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which abundantly forms on a substantially continuous basis attractive blossoms that are Orient Pink suffused with Aureolin Yellow on the upper surface and Dawn Pink suffused with Aureolin Yellow on the under surface. Such blossoms additionally display a vervain lemon-scented fragrance. The foliage is dark green and exhibits a glossy upper surface that contrasts well with the light-colored blossoms. The plant exhibits a vigorous, compact and bushy growth habit. The new variety is well suited for growing as attractive ornamentation in the landscape.

1 Drawing Sheet

SUMMARY OF THE INVENTION

The new variety of Floribunda rose plant was created by artificial pollination wherein two parents were crossed which previously had been studied in the hope that they would contribute the desired characteristics. The female parent (i.e., the seed parent) of the new variety was the 'Flamingo' variety (non-patented in the United States). The male parent (i.e., the pollen parent) of the new variety was the product of the pollination of the 'Meihartfo' variety (non-patented in the United States) and the 'Tip Top' variety (non- patented in the United States). The 'Meihartfo' variety sometimes is known as the, 'Pink Wonder' variety and the 'Tip Top' variety sometimes is known as the 'Baby Doll' variety. The parentage of the new variety can be summarized as follows:

'Flamingo'×('Meihartfo'×'Tip Top').

The seeds resulting from the above pollination were sown and small plants were obtained which were physically and biologically different from each other. Selective study resulted in the identification of a single of the new variety.

It was found that the new variety of Floribunda rose plant of the present invention possesses the following combination of characteristics:

(a) forms in abundance on a substantially continouous basis attractive fragrant blossoms that are light Orient Pink suffused with Aureolin Yellow on the upper surface and Dawn Pink suffused with Aureolin Yellow on the under surface,
(b) forms attractive vigorous dark green foliage having a glossy upper surface,
(c) exhibits a vigorous, compact and bushy growth habit,
(d) exhibits a particularly good disease resistance against black spot, and
(e) is well suited for growing as attractive ornamentation in the landscape.

As demonstrated in France, the new variety undergoes asexual propagation by a number of routes, including budding, grafting, cuttage, etc. The characteristics of the new variety have been found to be strictly transmissible by such asexual propagation from one generation to another in France.

The new variety has been named the 'Meioffic' variety.

BRIEF DESCRIPTION OF PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelii* understock and growing outdoors at Le Cannet des Maures, Var, France. Dimensions in centimeters are shown at the bottom of the photograph.

Fig. 13 illustrates a specimen of an adult main branch;

DETAILED DESCRIPTION

Figures 1, 2, 3, 4, 5, 6, 7, 8, 9, 10, 11, 12, 14, 15, 16:
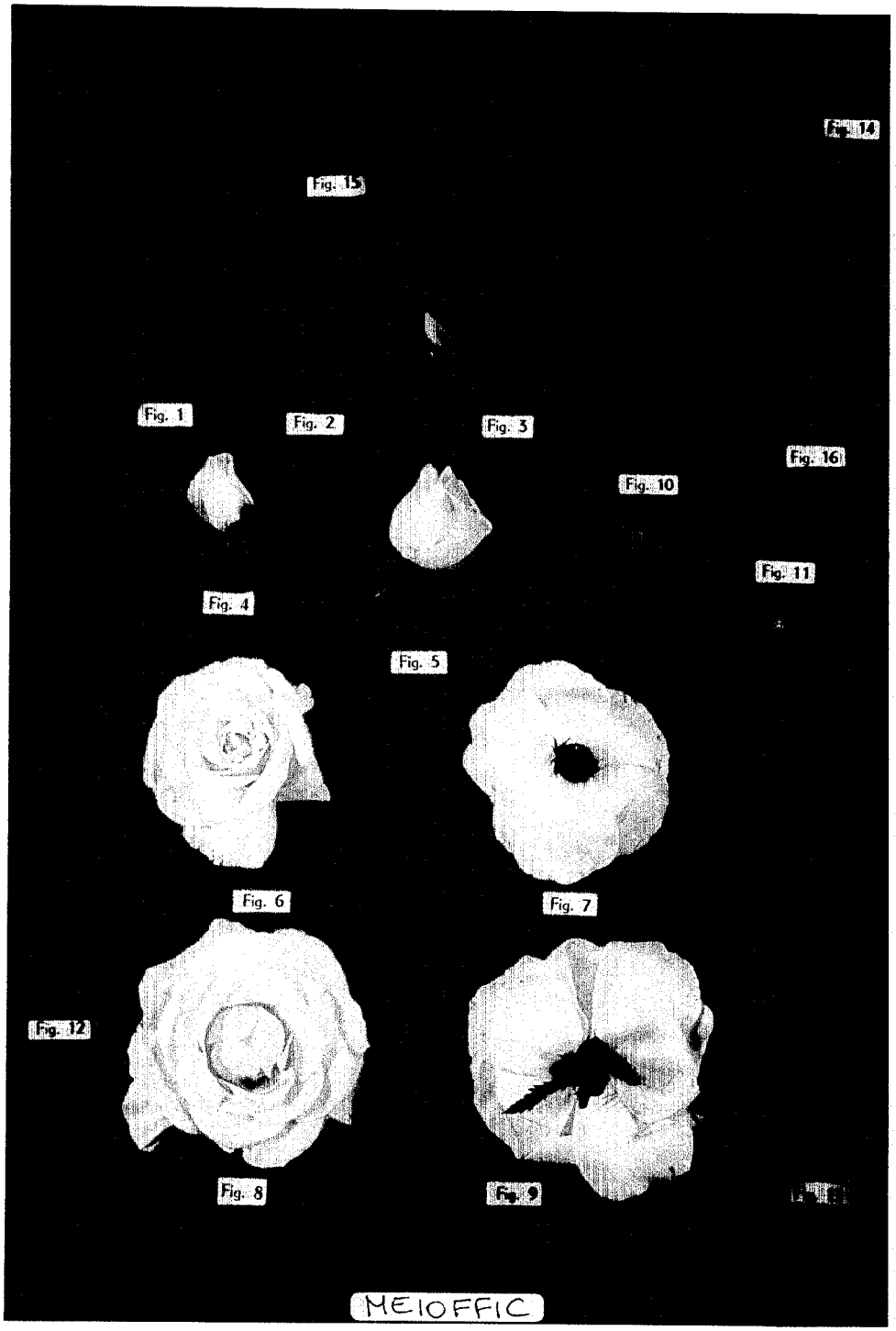
Fig. 1 illustrates a specimen of a young shoot.
Fig. 2 illustrates a specimen of a floral bud before the opening of the sepals.
Fig. 3 illustrates a specimen of a floral bud at the opening of the sepals.
Fig. 4 illustrates a specimen of a floral bud at the opening of the petals.
Fig. 5 illustrates a specimen of a flower in the course of opening.
Fig. 6 illustrates a specimen of an open flower—plan view—obverse.
Fig. 7 illustrates a specimen of an open flower—plan view—reverse.
Fig. 8 illustrates a specimen of a fully open flower—plan view—obverse.
Fig. 9 illustrates a specimen of a fully open flower—plan view—reverse.
Fig. 10 illustrates a specimen of a floral receptacle showing the arrangement of the stamens and pistils.
Fig. 11 illustrates a specimen of a floral receptacle showing the arrangement of the pistils (stamens removed)
Fig. 12 illustrates a specimen of a flowering stem.
Fig. 14 illustrates a specimen of a leaf with three leaflets—plan view—upper surface.
Fig. 15 illustrates a specimen of a leaf with five leaflets—plan view—under surface.
Fig. 16 illustrates a specimen of a leaf with seven leaflets—plan view—upper surface.

The chart used in the identification of the colors is that of The Royal Horticultural Society (R.H.S. Colour Chart). The terminology which precedes reference to the chart has been added to indicate the corresponding color in more common terms. The description is based on two year-old specimens of the new variety during June while budded on *Rosa froebelii* understock and growing outdoors at Le Cannet des Maures, Var, France.

Class: Floribunda.

Plant:

*Height.*—Approximately 50 to 60 cm. on average at the end of the growing season.

*Habit.*—Bushy.

Branches:

*Color.*—Young stems: light green, Yellow-Green Group 146C. Adult wood: medium green, Yellow-Green Group 146B.

*Thorns.*—Size: medium. Quantity: numerous. Color: pinkish on young stems, and Havana brown on mature wood (as illustrated).

Leaves:

*Stipules.*—Adnate, pectinate, wide and linear.

*Petioles.*—Upper surface: striped reddish on young foliage and medium green on adult foliage with more or less glandular edges. Under surface: light green, with some small thorns.

*Leaflets.*—Number: 3, 5 (most often), and 7. Shape: oval. Serration: single and regular (as illustrated). Texture: consistent. General appearance: dense, and glossy foliage. Color (young foliage): Upper surface: Yellow-Green Group 146A, and more or less stained with reddish coloration. Under surface: medium green, Yellow- Green Group 146B and widely stained with reddish coloration. Color (adult foliage): Upper surface: Yellow-Green Group 146 A. Under surface: light green, Yellow-Green Group 146D.

Inflorescence:

*Number of flowers.*—Usually one to seven blooms per stem.

*Peduncle.*—Light green and more or less stained with reddish coloration, and approximately 5 cm. in length on average.

*Sepals.*—Upper surface: tomentose and greenish in coloration. Under surface: medium green in coloration and commonly with some extensions.

*Buds.* —Shape: oval. Length: approximately 2.5 cm. on average. Size: medium. Color upon opening: Upper surface: near Orient Pink, Red Group 36 A, and more or less suffused with Aureolin Yellow, Yellow Group 12B. Under surface: near Dawn Pink, Red Group 49A, and suffused with Aureolin Yellow, Yellow Group 12B.

*Flower.*—Shape: cup-shaped and elongated with a substantially round heart. Diameter: approximately 10 cm. on average. Color (when opening begins): Upper surface: near Orient Pink, Red Group 36A, and more or less suffused with Aureolin Yellow, Yellow Group 12B. Under surface: near Dawn Pink, Red Group 49A, and suffused with Aureolin Yellow, Yellow Group 12B. Color (when blooming): Upper surface: near Orient Pink, Red Group 36A, and more or less suffused with Aureolin Yellow, Yellow Group 12B. Under surface: near Dawn Pink, Red Group 49A, and suffused with Aureolin Yellow, Yellow Group 12B. Color (at end of opening): Upper surface: near Orient Pink, Red Group 36A, and more or less suffused with Aureolin Yellow, Yellow Group 12B. Under surface: near Dawn Pink, Red Group 49A, and suffused with Aureolin Yellow, Yellow Group 12B. Fragrance: medium, vervain lemon-scented. Lasting quality: very long-lasting blossoms. Petal drop: good with the petals commonly detaching cleanly. Petal form: rounded to oval. Petal number: approximately 40 to 45 on average. Stamen number: approximately 125 on average. Anthers: ochre in coloration. Filaments: bright yellow in coloration. Pistils: approximately 70 on average. Stigmas: yellowish in coloration. Styles: pinkish in coloration. Receptacle: medium green, smooth, and in longitudinal section in the shape of a pitcher.

Development:

*Vegetation.*—Vigorous.

*Blooming.*—Very abundant and substantially continuous.

*Resistance to diseases.*—Very good, particularly with respect to black spot.

*Resistance to frost.*—Very good.

I claim:

1. A new and distinct variety of Floribunda rose plant characterized by the following combination of characteristics:

(a) forms in abundance on a substantially continuous basis attractive fragrant blossoms that are light Orient Pink suffused with Aureolin Yellow on the upper surface and Dawn Pink suffused with Aureolin Yellow on the under surface, (b) forms attractive vigorous dark green foliage having a glossy upper surface, (c) exhibits a vigorous, compact and bushy growth habit, (d) exhibits particularly good disease resistance against black spot, and (e) is well suited for growing as attractive ornamentation in the landscape;

substantially as herein shown and described.

* * * * *

MEIOFFIC